United States Patent [19]
Suh et al.

[11] Patent Number: 6,077,928
[45] Date of Patent: Jun. 20, 2000

[54] BIS(DIALKYLMALEIMIDE) DERIVATIVE AND POLYETHERIMIDE FOR OPTICAL COMMUNICATIONS FORMED THEREFROM

[75] Inventors: Dong-hack Suh, Daejeon; Eun-young Chung, Chungcheongnam-do; Tae-hyung Rhee, Sungnam, all of Rep. of Korea

[73] Assignee: SamSung Electronics Co., Ltd., Suwon, Rep. of Korea

[21] Appl. No.: 09/223,313

[22] Filed: Dec. 30, 1998

[30] Foreign Application Priority Data

Dec. 31, 1997 [KR] Rep. of Korea ............. 97/82006

[51] Int. Cl.$^7$ ................................. C08G 73/10
[52] U.S. Cl. .................. 528/170; 528/170; 528/310; 528/322; 528/332; 548/462
[58] Field of Search ............. 548/462; 528/310, 528/170, 322, 332

[56] References Cited

U.S. PATENT DOCUMENTS

| | | | |
|---|---|---|---|
| 3,920,697 | 11/1975 | Takeoshi | 548/462 |
| 4,087,441 | 5/1978 | Lee | 548/462 |
| 4,197,133 | 4/1980 | Zweifel et al. | 548/462 |
| 5,089,628 | 2/1992 | Maruta | 548/521 |
| 5,554,765 | 9/1996 | Ohta et al. | 548/462 |

FOREIGN PATENT DOCUMENTS

| | | |
|---|---|---|
| 2005669A1 | 4/1969 | France . |
| 5230018 | 9/1993 | Japan . |
| 1181255 | 5/1967 | United Kingdom . |

Primary Examiner—P. Hempton-Hightower
Attorney, Agent, or Firm—Robert E. Bushnell, Esq.

[57] ABSTRACT

A bis(disubstitutedmaleimide) derivative and a polyetherimide for optical communications and the polyetherimide formed therefrom are described. The polyetherimde has a high refractive index, so that when using such polyetherimide as a material for a core of an optical fiber, the range of the materials that can be selected for the cladding becomes wide. Also, a coating property and adhesion to a substrate are improved, thereby providing a good film forming property and thermal stability. Also, because the polyetherimide can minimize optical loss at a near infrared wavelength range, the polyetherimide is very useful as an optical material in the optical communications field adopting the light of near infrared wavelength.

16 Claims, No Drawings

BIS(DIALKYLMALEIMIDE) DERIVATIVE AND POLYETHERIMIDE FOR OPTICAL COMMUNICATIONS FORMED THEREFROM

BACKGROUND OF THE INVENTION

1. Field of the Invention

The present invention relates to a new material for optical communications, and more particularly, to a polyetherimide for optical communications, which minimizes optical loss in a near infrared wavelength range, and has good thermal stability and film processing properties.

2. Description of the Related Art

A wavelength range for optical communications has been shifted from 800 nm to 1550 nm, which corresponds to the near infrared wavelength range. Thus, it is ideal to manufacture an optical communication device using a material which barely absorbs light belonging to the wavelengths of the near infrared wavelength range.

A polymer is generally used for an optical substrate such as an optical lens or compact disk. Recently, many attempts have been made to use such polymers as optical waveguide materials for light transfer in the near infrared wavelength range.

A conventional polymer generally absorbs light of 1000–1700 nm which corresponds to the near infrared wavelength range. Such absorption of light in the near infrared wavelength range by the polymer is caused by overtone of harmonics due to stretching and deformation vibrations of carbon-hydrogen (C—H) bonds in alkyl, phenyl and other similar functional groups. Thus, it is not desirable to use the conventional polymer as the optical waveguide material utilizing the light of the near infrared wavelength range because of a large optical loss. In order to reduce the optical loss, light absorption wavelength region of a polymer must be shifted from the near infrared wavelength range to a longer or shorter wavelength region. To this end, a method in which hydrogen in the C—H bond is substituted by fluoride (F) or deuterium (D) has been suggested.

Particularly, in the case of substituting hydrogen with deuterium, since a C—D bond causes the light absorption at the wavelength range of 1500 nm, it is not suitable for materials for optical communications devices using 1500 nm wavelengths. On the other hand, substitution of hydrogen by fluorine can minimize optical loss in light absorption at the wavelengths in the range of 1000–1700 nm.

An optical material used for fabricating optical devices such as an opto-electronic integrated circuit (OEIC), an opto-electrical mixed wiring board (OEMWB), a hybrid integration device, a plastic optical fiber or a multi-chip module (MCM) must have good thermal stability during a fabrication process, particularly at a temperature of about 250° C. Since the thermal stability of an optical material is a very important factor, careful consideration must be taken of the glass transition temperature, thermal decomposition temperature, thermal expansion coefficient or birefringence of the optical material.

A polyimide has been most widely known as a polymer having good thermal stability. Since the polyimide is stable at a high temperature of about 400° C., great efforts to utilize polyimide as a material for optical communications have been consistently made.

However, generally, since a conventional polyimide has many C—H bonds in its molecular structure, it exhibits a large optical loss in the near infrared region. To overcome such a problem, recently, a method in which hydrogen in C—H bonds of a polyimide is partially or entirely substituted by fluorine has been proposed.

However, if hydrogen is substituted by fluorine, the refractive index of the polymer is decreased. Here, the content of fluorine in the polymer is proportional to the decreased level of the refractive index. Thus, since a polyimide obtained by substituting hydrogen in the C—H bonds by fluorine, that is, a fluorinated polyimide, has a low refractive index, in the case of using the same as a core, the range of selection of a material capable of being used for cladding becomes narrow.

Also, the higher the content of fluorine in the polyimide is, the lower the surface tension of a composition containing the polyimide is. Thus, it is difficult to coat such a composition on a substrate and the adhesion of a film comprised of the composition is poor. As a result, film characteristics are deteriorated and the film formed thereby is easily fragile. Thus, it is very difficult to put the polyimide into practical use for an optical communications material.

SUMMARY OF THE INVENTION

Therefore it is an object to the president mentioned to provide improved optical polymer material.

It is a further object of the present invention to provide an improved optical polymer material for use with near infrared light.

It is a still further object to provide an optical polymer material with low light loss at near infrared wavelengths.

It is a yet further object to provide an optical material with high thermal stability.

It is a still yet further object to provide an optical material with a suitable refractive index for use in an optical fiber.

It is another object to provide an optical material with suitable adhesion characteristics for preparation of optical films.

It is still another object to provide an optical material which is suitable for use in an optical device such as an opto-electronic integrated circuit.

It is yet another object to provide an optical material with excellent processing characteristics and robustness.

To solve the above problems, it is an object of the present invention to provide a polyetherimide for optical communications, which minimizes light loss in a near infrared wavelength of 1,000~1,700 nm and has good thermal stability at 200° C. or higher and good film processing properties, and an intermediate for synthesizing the same.

According to an aspect of the present invention, there is provided a bis(disubstitutedmaleimide) derivative represented by the chemical formula (1):

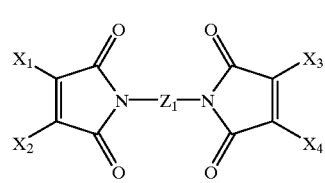

(1)

wherein $X_1$, $X_2$, $X_3$ and $X_4$ are independently selected from the group consisting of halogen atom, halogenated alkyl group, halogenated aromatic ring group,—$NO_2$, —$OR^1$ and $SR^1$ (where $R^1$ is halogenated alkyl or halogenated aromatic ring group); and $Z_1$ is selected from the group consisting of divalent halogenated aliphatic hydrocarbon, divalent halogenated aliphatic cyclic hydrocarbon and divalent halogenated aromatic hydrocarbon.

Preferably, the $X_1$, $X_2$, $X_3$ and $X_4$ are independently selected from the group consisting of partially or perchlorinated alkyl groups, partially or perchlorinated aromatic ring groups, partially or perchlorinated alkoxy groups, and partially or perchlorinated phenoxy groups.

According to another aspect of the present invention, there is provided a polyetherimide for optical communications, comprising repeating unit represented by the chemical formula (2):

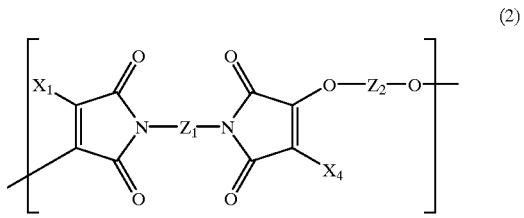

(2)

wherein $X_1$, and $X_4$ are independently selected from the group consisting of halogen atom, halogenated alkyl group, halogenated aromatic ring group, $NO_2$, $-OR^1$ and $-SR^1$ (where $R^1$ is halogenated alkyl or halogenated aromatic ring group); and $Z_1$ and $Z_2$ are independently selected from the group consisting of divalent halogenated aliphatic hydrocarbon, divalent halogenated aliphatic cyclic hydrocarbon and divalent halogenated aromatic hydrocarbon.

Preferably, $X_1$ and $X_4$ are radicals independently selected from the group consisting of chlorine atom, partially or perchlorinated alkyl groups, partially or perchlorinated aromatic ring groups, partially or perchlorinated alkoxy groups, and partially or perchlorinated phenoxy groups.

Also, preferably, $Z_1$ and $Z_2$ are independently selected from the group consisting of divalent halogenated aliphatic hydrocarbon of $C_1$–$C_{25}$, divalent halogenated aliphatic cyclic hydrocarbon of $C_1$–$C_{25}$ and divalent halogenated aromatic hydrocarbon of $C_6$–$C_{25}$. More preferably, $Z_1$ and $Z_2$ are independently selected from the group represented by the following structural formulae:

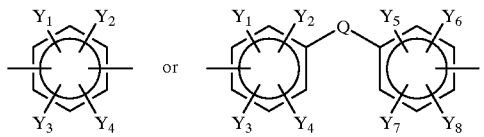

wherein $Y_1$, $Y2$, $Y_3$, $Y_4$, $Y_5$, $Y6$, $Y_7$ and $Y8$ are independently selected from the group consisting of halogen atom, halogenated alkyl group, halogenated aromatic ring group, $NO_2$, $-OR^1$ and $-SR^1$ (where $R^1$ is halogenated alkyl or halogenated aromatic ring group); and Q is either a single chemical bond or is selected from the group consisting of $-O-$, $-CO-$, $-SO_2-$, $-S-$, $-(OT)_m-$, $-(OT)_m-$ and $-(OT)-$ (where T is halogenated alkylene or halogenated arylene group and m is an integer from 1 to 10).

DESCRIPTION OF THE PREFERRED EMBODIMENTS

A bis(disubstitutedmaleimide) derivative represented by the chemical formula (1) is usable as an intermediate for synthesizing a polyetherimide for optical communications. In the polyetherimide for optical communications according to the present invention, hydrogen of C—H bond is substituted with halogen atom or nitro group. Here, the halogen atom substituted for the hydrogen is not limited to a specific halogen atom, and combinations of various halogen atoms are possible.

Preferably, the hydrogen of C—H bond of the polyetherimide is substituted with chloride (Cl). This is because the optical loss caused by a C—Cl bond is relatively less than that by the C—H bond.

Hereinafter, a method for synthesizing the bis (dialkylmaleimide) derivative according to the present invention will be described with reference to the reaction formula (3).

First, a diamine compoud (B) is reacted with maleic anhydride, resulting in a bis(maleimide) derivative. Then, the bismaleimide derivative is reacted with a halogenated compound or nitric acid to synthesize a bis (disubstitutedmaleimide) derivative.

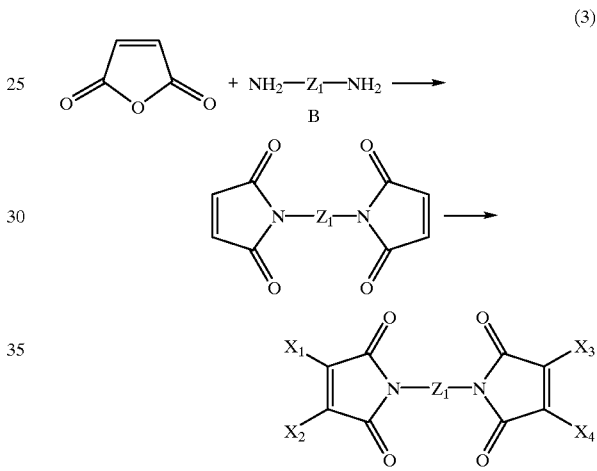

(3)

In the reaction formula (3), $Z_1$ is divalent halogenated aliphatic hydrocarbon, divalent halogenated aliphatic cyclic hydrocarbon or divalent halogenated aromatic hydrocarbon, $X_1$, $X_2$, $X_3$ and $X_4$ are independently selected from the group consisting of halogen atom, halogenated alkyl group, halogenated aromatic ring group, $NO_2$, $-OR^1$ and $-SR^1$ (where $R^1$ is halogenated alkyl or halogenated aromatic ring group).

The reaction process will be described in detail. After dissolving maleic anhydride in acetic acid at 0~50° C., a diamine compound dissolved in acetic acid is added dropwise into the mixture. The reaction mixture is stirred for 0.5~24 hours under nitrogen ($N_2$), and then heated at 130° C. for 15~24 hours, resulting in a bismaleimide derivative.

Thionyl chloride and pyridine are added to the bismaleimide derivative, reacted at 0~50° C. for 2~48 hours, and then reacted again at 80~100° C. for 24~72 hours, resulting in a bis(dichloromaleimide) derivative. Additional reactions or other treatment of the bismaleimide derivative may be used to produce other bis(disubstitutedmalelimide) derivatives.

The diamine compound (B) is not limited to a specific compound. For example, the diamine compound (B) may be bis(perfluorophenyl)alkanes, bis(perfluorophenyl)sulfones, bis(perfluorophenyl)ethers or α,α'-bis(perfluorophenyl) diisopropylbenzenes. In detail, the diamine compound (B)

includes tetrafluoro-1,2-phenylenediamine, tetrafluoro-1,3-phenylendiamine, tetrafluoro-1,4-phenylenediamine, tetrachloro-1,2-phenylenediamine, tetrachloro-1,3-phenylenediamine, tetrachloro-1,4-phenylenediamine, hexafluoro-1,5-diaminonaphthalene, hexafluoro-2,6-diaminonaphthalene, 3-trifluoromethyltrifluoro-1,2-phenylenediamine, 4-trifluoromethyltrifluoro-1,2-phenylenediamine, 2-trifluoromethylfluoro-1,3-phenylenediamine, 4-trifluoromethyltrifluoro-1,3-phenylenediamine, 5-trifluoromethyltrifluoro-1,3-phenylenediamine, 2-trifluoromethyltrifluoro-1,4-phenylenediamine, 3-pentafluoroethyltrifluoro-1,2-phenylenediamine, 4-pentafluoroethyltrifluoro-1,2-phenylenediamine, 2-pentafluoroethyltrifluoro-1,3-phenylenediamine, 4-pentafluoroethyltrifluoro-1,3-phenylenediamine, 5-pentafluoroethyltrifluoro-1,3-phenylenediamine, 2-pentafluoroethyltrifluoro-1,4-phenylenediamine, 3,4-bis(trifluoromethyl)difluoro-1,2-phenylenediamine, 3,5-bis(trifluoromethyl)difluoro-1,2-phenylenediamine, 2,4-bis(trifluoromethyl)difluoro-1,3-phenylenediamine, 4,5-bis(trifluoromethyl)difluoro-1,3-phenylenediamine, 2,3-bis(trifluoromethyl)difluoro-1,4-phenylenediamine, 2,5-bis(trifluoromethyl)difluoro-1,4-phenylenediamine, 3,4-bis(trifluoromethyl)-difluoro-1,2-phenylenediamine, 3-trifluoromethoxytrifluoro-1,2-phenylenediamine, 4-trifluoromethoxytrifluoro-1,2-phenylenediamine, 2-trifluoromethoxytrifluoro-1,3-phenylenediamine, 4-trifluoromethoxytrifluoro-1,3-phenylenediamine, 5,-trifluoromethoxytrifluoro-1,3-phenylenediamine, 2-trifluoromethoxytrifluoro-1,4-phenylenediamine, 3,4,5-tris(trifluoromethyl)fluoro-1,2-phenylenediamine, 3,4,6-tris(trifluoromethyl)fluoro-1,2-phenylenediamine, 2,4,5-tris(trifluoromethyl)fluoro-1,3-phenylenediamine, 2,4,6-tris(trifluoromethyl)-fluoro-1,3-phenylenediamine, 4,5,6-tris(trifluoromethyl)fluoro-1,3-phenylenediamine, tetrakis(trifluoromethyl)-1,2-phenylenediamine, tetrakis(trifluoromethyl)-1,3-phenylenediamine, tetrakis(trifluoromethyl)1,4-phenylenediamine, 3,3'-diaminooctafluorobiphenyl, 3,4'-diaminooctafluorobiphenyl, 4,4'-diaminooctafluorobiphenyl, 3,3'-diaminooctachlorobiphenyl, 3,4'-diaminooctachlorobiphenyl, 4,4'-diaminooctachlorobiphenyl, 2,2'-bis(trichloromethyl)-4,4'-diaminohexachlorobiphenyl, 3,3'-bis(trichloromethyl)-4,4'-diaminohexafluorobiphenyl, bis(4-aminotetrafluorphenyl)dichloromethane, 1,2-bis(4-aminotetrafluorophenyl)tetrachloroethane, 2,2'-bis(4-aminotetrafluorophenyl)hexachloropropane, 2,2'-bis(trifluoromethyl)-4,4'-diaminohexachlorobiphenyl, 3,3'-bis(trifluoromethyl)-4,4'-diaminohexafluorobiphenyl, bis(4-aminotetrafluorophenyl)difluoromethane, 1,2-bis(4-aminotetrafluorophenyl)tetrachloroethane, 2,2'-bis(4-aminotetrafluorophenyl)hexafluoropropane, bis(3-aminotetrafluorophenyl)ether, 3,4'-diaminooctafluorobiphenylether, bis(4-aminotetrafluorophenyl)ether, bis(3-aminotetrachlorophenyl)ether, 3,4'-diaminooctachlorobiphenylether, bis(4-aminotetrachlorophenyl)ether, 3,3'-diaminooctafluorobenzophenone, 3,4'-diaminooctafluorobenzophenone, 4,4'-diaminooctafluorobenzophenone, bis(3-aminotetrafluorophenyl)sulfone, 3,4'-diaminooctafluorobiphenylsulfone, bis(4-aminotetrafluorophenylsulfone), bis(3-aminotetrafluorophenyl)sulfide, 3,4'-diaminooctafluorobiphenylsulfide, bis(4-aminotetrafluorophenyl)sulfide, 4-aminotetrafluorophenoxy-4'-aminotetrafluorophenyldifluoromethane, bis(4-aminotetrafluorophenoxy)difluoromethane, 1,2-bis(4-aminotetrafluorophenoxy)tetrafluoroethane, 2,2-bis(4-aminotetrafluorophenoxy)hexafluoropropane, bis(4-aminotetrafluorophenoxy)dichloromethane, 1,2-bis(4-aminotetrafluorophenoxy)tetrachloroethane, 2,2-bis(4-aminotetrafluurophenoxy)hexachloropropane, 4,4"-diaminododecafluoro-p-terphenyl, 2',3'-bis(trifluoromethyl)-4,4"-diamino-p-terphenyl, 2,2"-bis(trifluoromethyl)-4,4"-diamino-p-terphenyl, 2',5'-bis(trifluoromethyl)-4,4"-diaminotelphenyl, 2,7-diaminohexafluorodibenzofuran, 1,4-bis(4-aminotetrafluorophenoxy)tetrafluorobenzene, 2,6-diaminohexafluoronaphthalene, 2,7-diaminooctafluorophenanthrene, 2,6-diaminooctafluoroanthracene, 2,7-diaminohexathianthrene, 2,6-diaminohexafluoroanthraquinone, 2,6-diaminohexafluorobiphenylene, 2,6-diaminooxtafluoroanthrone, 2,7-diaminotetrafluorodibenz[b,e]1,4-dioxane, 2,2'-bis(4-aminophenyl)hexafluoropropane, 2,2'-bis(4-aminophenyl)hexachloropropane, 2,4-diaminobenzotrifluoride, 2,2-bis(trifluoromethyl)benzidine, 2,2-bis[4-(4-amino-2-trifluorophenoxy)phenyl]hexafluoropropane, 2,2-bis[4-(4-amino-2-trifluorophenoxy)phenyl]hexachloropropane, 3,4-diaminobenzotrifluoride, 3,5-diaminobenzotrifluoride, 2,5-diaminobenzotrifluoride, 2,2-bis[4-(4-aminophenoxy)phenyl]hexafluoropropane, 2,2-bis[4-(4-aminophenoxy)phenyl]hexachloropropane, or 3,4-diamino-1-fluorobenzene.

A method for synthesizing a polyetherimide according to the present invention using the bis(disubstitutedmaleimide) derivative represented by the chemical formula (1) as a starting material will be described.

First, the bis(disubstitutedmaleimide) represented by the chemical formula (1) and a diol compound (HO-$Z_2$-OH, where $Z_2$ is a divalent halogenated aliphatic hydrocarbon, divalent halogenated aliphatic cyclic hydrocarbon or divalent halogenated aromatic hydrocarbon) are dissolved in an organic solvent, and then reacted at 0~100° C. for 2~240 hours. Here, the organic solvent may be a N,N-dimethylformamide, N-methyl-2-pyrrolidone or N,N-dimethylformamide.

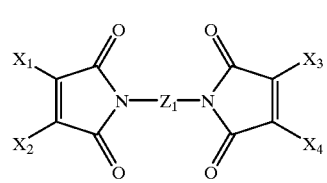

(1)

In the chemical formula (1), $X_1$, $X_2$, $X_3$ and $X_4$ and $Z_1$ are the same as those described above.

After precipitating the reaction mixture using an organic solvent such as methyl alcohol, the resultant precipitate is separated by filtering. Then, the precipitate is dried, resulting in a polyetherimide having repeating unit represented by the chemical formula (2).

The polyesterimide obtained through the above process has a molecular weight of $1\times10^4$~$4.5\times10^4$ Dalton. Here, the molecular weight is measured using gel permeation chromatography.

A thermal decomposition temperature of the polyetherimide, measured by thermogravimetry analysis (TGA), is 300~500° C., preferably, 375~425° C. Also, the glass transistion temperature of the polyetherimide is 220~320° C.

The diol compound (C) is not limited to a specific compound. For example, the diol compound (C) may be bis(perfluorophenyl)alkanes, bis(perfluorophenyl)sulfones, bis(perfluorophenyl)ethers or α,α'-bis(perfluorophenyl) diisopropylbenzenes. In detail, the diol compound (C) includes hexafluoro-1,5-pentanediol, 2,2,3,3,4,4,5,5-octafluorohexane-1,6-diol, 2,2,3,3-tetrafluorobutane-1,4-diol, 2,2,3,3,4,4,5,5,6,6,7,7-dodecafluoro-1,1-heptanediol, 2,2,3,3,4,4,5,5,6,6,7,7-dodecafluoro-1,8-octane-diol, 3,3,4,4,5,5,6,6-octafluorooctane-1,8-diol, 2,2,3,3,4,4,5,5,6,6,7,7,8,8-tetradecafluorononane, 1H, 1H, 2H, 3H, 3H-perfluorononane-1,2-diol, 7H-dodecafluoro-1,1-heptanediol, 1H, 1H, 10H, 10H-hexadecafluorodecane-1,10-diol, 1H, 1H, 10H, 10H-perfluorodecane-1,10-diol, 1H, 1H, 2H, 3H, 3H-perfluorodecane-1,2-diol, tetrafluoronone-1,9-diol, tetrafluorohydroquinone, tetrachlorohydroquinone, 2,2-bis(3-amino-4-hydroxyphenyl) hexafluoropropane, 2,2-bis(3-amino-4-hydroxyphenyl)hexachloropropane, 2,2-bis[4-(2-hydroxyethoxy)phenyl]hexafluoropropane, 2,2-bis[4-(2-hydroxyethoxy)phenyl]hexachloropropane, 1,3-bis(2-hydroxyhexafluoroisopropyl)benzene, 1,4-bis(2-hydroxyhexafluoroisopropyl)benzene, 4,4'-bis(2-hydroxyhexafluoroisopropyl)diphenyl, 4,4'-bis(2-hydroxyhexafluoroisopropyl)diphenylether, 2,2-bis(4-hydroxypheny)lexafloropropane, 1,3-bis(2-hydroxyhexachloroisoporpyl)benzene, 1,4-bis(2-hydroxyhexachloroisopropyl)benzene, 4,4'-bis(2-hydroxyhexachloroisopropyl)diphenylether, 2,2'-bis(4-hydroxyphenyl)hexachloropropane, 1,1-(4,4'-dihydroxydiphenyl)ethane, 1,2-(4,4'-dihydroxydiphenyl) ethane, 1,10-(4,4'-dihydroxydiphenyl)decane, 1,4-(4,4'-dihydroxydiisopropylidenediphenyl)benzene, 1,4-(4,4'-dihydroxydimethylenediphenyl)benzene, 1,10-(4,4'-dihydroxydiphenyl)-1,1-dioxodecane, 4,4'-dihydroxydiphenylether, 4,4'-dihydroxydiphenylsulfide, 4,4'-dihydroxy-3,3'-dimethyldiphenylsulfide, 4,4'-dihydroxydiphenylsulfoxide, 4,4'-dihydroxydiphenylsulfone, 4,4'-dihydroxy-3,3'-dichlorodiphenylsulfone, 4,4'-dihydroxydiphenyl-1,1-butane, 4,4'-dihydroxydiphenyl-1,1-isobutane, 4,4'-dihydroxydiphenyl-1,1-cyclopentane, 4,4-dihydroxydiphenyl-1,1'-cyclohexane, 4,4'-dihydroxydiphenyl-2,2-butane, 4,4'-dihydroxydiphenyl-2,2-pentane, 4,4'-dihydroxydiphenyl-2,2-(4-methylpentane), 4,4'-dihydroxydiphenyl-4,4-heptane, 4,4'-dihydroxydiphenyl-2,2,2-ethane, 4,4-dihydroxytriphenylmethane, 4,4'-dihydroxy-3,3',5,5'-tetrachlorodiphenyl-1,1-cyclohexane, 4,4'-dihydroxydiphenyl-2,2-hexane, 4,4-dihydroxydiphenyl-β,β-decahydronaphthalene, 4,4'-dihydroxydiphenylmethane, 4,4'-dihydroxydiphenyl-2,2-propane, 4,4'-dihydroxy-3,3',5,5'-tetrachlorodiphenyl-2,2-propane, 4,4'-dihydroxy-3,3'-dichlorodiphenyl-2,2-propane, 4,4'-dihydroxy-3,3'-dimethyldiphenyl-2,2-propane, 1,3-propanediol, 1,4-butanediol, 1,1'-dihydroxydiethylether, 1,1'-dihydroxydimethyl-2,2-propane, 1,1'-dihydroxydimethyl-2,2-pentane, 1,1'-dihydroxydimethyl-1,4-benzene, 1,1'-dihydroxydiethylbenzene, 1,1'-dihydroxydimethylbenzidine, 1,1'-dihydroxydiethylbenzidine, (1,1'-biphenyl)-2,5-diol, (1,1'-biphenyl)-4,4'-diol, (1,1'-biphenyl)-3,4-diol, (1,1'-biphenyl)-3,4'-diol, (1,1'-biphenyl)-2,2'-diol, (1,1'-biphenyl)-3,3'-diol, (1,1'-biphenyl)-2,4'-diol, 3,3'-dimethyl-(1,1'-biphenyl)-4,4'-diol, 5,5'-dimethyl-(1,1'-biphenyl)-2,2'-diol, 3,3'-dimethyl-(1,1'-biphenyl)-2,2'-diol, 6,6'-dimethyl-(1,1'-biphenyl)-2,2'-diol, 5,5'-diethyl-(1,1'-biphenyl)-2,2'-diol, 3,3'-difluoro-(1,1'-biphenyl)-4,4'-diol, 5,5'-difluoro-(1,1'-biphenyl)-2,2'-diol, 3,3'-dimethyl-(1,1'-biphenyl)-2,2'-diol, 3,3'-dimethyl-(1,1'-biphenyl)-4,4'-diol, 6,6'-dimethyl-(1,1'-biphenyl)-2,2'-diol, 6,6'-dimethyl-(1,1'-biphenyl)-3,3'-diol, 5,6'-dimethyl 6,-dimethyl-(1,1'-biphenyl)-2,3'-diol, 3,3',5,5'-tetrafluoro-(1,1'-biphenyl)-2,2'-diol, 3,3',5,5'-tetramethoxy-(1,1'-biphenyl)-4,4'-diol, 2,2',6,6'-tetramethoxy-(1,1'-biphenyl)-4,4'-diol, 3,3',5,5'-tetramethyl-(1,1'-biphenyl)-4,4'-diol, 3,3',5,5'-tetramethyl-(1,1'-biphenyl)-2,2'-diol, 2,2-bis(4-hydroxyphenyl)-1,3-perfluoropropane, 4,4'-dihydroxybenzophenone, 1,4-bis(4-hydroxyphenyl)benzene, 4,4'-bis(4"-hydroxybenzenesulfonyl)diphenyl, 4,4'-dihydroxy-3,3',5,5'-tetramethyldiphenyl-1,1'-methane, 2,2'-bis(4-hydroxy-2,3,5-trichlorophenyl)propane, 4,4'-dihydroxy-3,3',5,5'-tetramethyldiphenyl-1,1-methane, 2,2-bis(4-hydroxy-2,3,5-trichlorophenyl)propane, 4,4'-hydroxy-3,3',5,5'-tetramethyldiphenyl-1,1-cyclohexane, 1,1-bis(4-hydroxy-3-methyl)cyclohexane, 2,4-bis(4-hydroxyphenyl)2-methylbutane, 4,4'-dihydroxy-3,3',5,5'-tatramethyldiphenyl-1,1-sulfone, 2,2-bis(3-hydroxyphenyl)-1,3-perfluoropropane, 4,4'-dihydroxydiphenyl-1,1'-diphenylmethane, 2-bis(4-hydroxyphenyl)-1,1',3,3'-chlorodifluoropropane, 4,4'-dihydroxydiphenyl-1,1'-cyclopentane, 2-methylhydroxyquinone, 4,4'-dihydroxydiphenyl-2,2'-dichloro-1,1'-ethene, or 1,4-bis(4-hydroxyphenyl-2-propyl)benzene.

Hereinafter, the present invention will be described through the following examples.

However, the present invention is not limited to the following examples.

MONOMER EXAMPLE 1

A mixture of 0.0015 mol of 2,3,5,6-tetrafluorobenzenebismaleimide, 0.13 mol of thionyl chloride and 0.006 mol of pyridine was reacted.

The resulting mixture was evaporated in a vacuum to remove the solvent, and then washed with distilled water several times. The resulting product was dried at 80° C. for 24 hours, resulting in 2,3,5,6-tetrafluorobenzenebis (dichloromaleimide) (yield: 85%).

MONOMER EXAMPLE 2

A mixture of 0.0015 mol of 2,3,5,6-tetrachlorobenzenebismaleimide, 0.13 mol of thionyl chloride and 0.006 mol of pyridine was reacted.

The resulting mixture was evaporated in a vacuum to remove the solvent, and then washed with distilled water several times. The resulting product was dried at 80° C. for 24 hours, resulting in 2,3,5,6-tetrachlorobenzenebis (dichloromaleimide) (yield: 82%).

MONOMER EXAMPLE 3

A mixture of 0.0006 mol of octafluorobiphenylbismaleimide, 0.54 mol of thionyl chloride and 0.0024 mol of pyridine was reacted.

The resulting mixture was evaporated in a vacuum to remove the solvent, and then washed with distilled water several times. The resulting product was dried at 80° C. for 24 hours, resulting in octafluorobiphenylbis (dichloromaleimide) (yield: 75%).

MONOMER EXAMPLE 4

A mixture of 0.0015 mol of octachlorobiphenylbismaleimide, 0.13 mol of thionyl chloride and 0.006 mol of pyridine was reacted.

The resulting mixture was evaporated in a vacuum to remove the solvent, and then washed with distilled water several times. The resulting product was dried at 80° C. for 24 hours, resulting in octachlorobiphenylbis(dichloromaleimide) (yield: 80%).

MONOMER EXAMPLE 5

A mixture of 0.0015 mol of 2,2'-bis(trichloromethyl)-4-4'-bis(maleimide)hexafluorobiphenyl, 0.13 mol of thionyl chloride and 0.006 mol of pyridine was reacted.

The resulting mixture was evaporated in a vacuum to remove the solvent, and then washed with distilled water several times. The resulting product was dried at 80° C. for 24 hours, resulting in 2,2'-bis(trichloromethyl)-4-4'-bis(dichloromaleimide)hexafluorobiphenyl (yield: 73%).

MONOMER EXAMPLE 6

A mixture of 0.0015 mol of bis(4-maleimidetetrafluorophenyl)difluoromethane, 0.13 mol of thionyl chloride and 0.006 mol of pyridine was reacted.

The resulting mixture was evaporated in a vacuum to remove the solvent, and then washed with distilled water several times. The resulting product was dried at 80° C. for 24 hours, resulting in bis(4-dichloromaleimidetetrafluorophenyl)difluoromethane (yield: 76%).

MONOMER EXAMPLE 7

A mixture of 0.0015 mol of 2,4-bis(trifluoromethyl)difluoro-1,3-phenylenebismaleimide, 0.13 mol of thionyl chloride and 0.006 mol of pyridine was reacted.

The resulting mixture was evaporated in a vacuum to remove the solvent, and then washed with distilled water several times. The resulting product was dried at 80° C. for 24 hours, resulting in 2,4-bis(trifluoromethyl)difluoro-1,3-phenylenebis(dichloromaleimide) (yield: 71%).

MONOMER EXAMPLE 8

A mixture of 0.0015 mol of bis(4-maleimide)octafluorobenzophenone, 0.13 mol of thionyl chloride and 0.006 mol of pyridine was reacted.

The resulting mixture was evaporated in a vacuum to remove the solvent, and then washed with distilled water several times. The resulting product was dried at 80° C. for 24 hours, resulting in bis(dichloro-4-maleimide)octafluorobenzophenone (yield: 68%).

MONOMER EXAMPLE 9

A mixture of 0.0015 mol of bis(3,4-maleimide)octafluorobiphenylsulfone, 0.13 mol of thionyl chloride and 0.006 mol of pyridine was reacted.

The resulting mixture was evaporated in a vacuum to remove the solvent, and then washed with distilled water several times. The resulting product was dried at 80° C. for 24 hours, resulting in bis(3,4-dichloromaleimide)octafluorobiphenylsulfone (yield: 62%).

POLYMER EXAMPLE 1

0.01 mol of 2,3,5,6-tetrafluorobenzenebis(dichloromaleimide), 0.01 mol of tetrafluorohydroquinone, 0.1 mol of anhydrous calcium oxide, $5 \times 10^{-5}$ mol of triethylamine and 5 ml of N,N-dimethylformamide were reacted under nitrogen atmosphere.

The resulting mixture was cooled down to room temperature and was then precipitated using methyl alcohol. The resulting precipitate was filtered, washed with methyl alcohol several times, and then dried in a vacuum oven set to 80° C. for 24 hours, resulting in polyetherimide (PEI) (1) (yield: 83%).

POLYMER EXAMPLE 2

0.01 mol of 2,3,5,6-tetrachlorobenzenebis(dichloromaleimide), 0.01 mol of tetrachlorohydroquinone, 0.1 mol of anhydrous calcium oxide, $5 \times 10^{-5}$ mol of triethylamine and 5 ml of N,N-dimethylformamide were reacted under nitrogen atmosphere.

The resulting mixture was cooled down to room temperature and was then precipitated using methyl alcohol. The resulting precipitate was filtered, washed with methyl alcohol several times, and then dried in a vacuum oven set to 80° C. for 24 hours, resulting in PEI (2) (yield: 85%).

POLYMER EXAMPLE 3

0.01 mol of 2,3,5,6-tetrafluorobenzenebis(dichloromaleimide), 0.01 mol of 2,2-bis-(4-hydroxyphenyl)hexachloropropane, 0.1 mol of anhydrous calcium oxide, $5 \times 10^{-5}$ mol of triethylamine and 5 ml of N,N-dimethylformamide were reacted under nitrogen atmosphere.

The resulting mixture was cooled down to room temperature and was then precipitated using methyl alcohol. The resulting precipitate was filtered, washed with methyl alcohol several times, and then dried in a vacuum oven set to 80° C. for 24 hours, resulting in PEI (3) (yield: 81%).

POLYMER EXAMPLE 4

0.01 mol of 2,3,5,6-tetrafluorobenzenebis(dichloromaleimide), 0.01 mol of 4,4'-dihydroxydiphenylether, 0.1 mol of anhydrous calcium oxide, $5 \times 10^{-5}$ mol of triethylamine and 5 ml of N,N-dimethylformamide were reacted under nitrogen atmosphere.

The resulting mixture was cooled down to room temperature and was then precipitated using methyl alcohol. The resulting precipitate was filtered, washed with methyl alcohol several times, and then dried in a vacuum oven set to 80° C. for 24 hours, resulting in PEI (4) (yield: 87%).

POLYMER EXAMPLE 5

0.01 mol of 2,3,5,6-tetrafluorobenzenebis(dichloromaleimide), 0.01 mol of 4,4'-dihydroxydiphenylsulfone, 0.1 mol of anhydrous calcium oxide, $5 \times 10^{-5}$ mol of triethylamine and 5 ml of N,N-dimethylformamide were reacted under nitrogen atmosphere.

The resulting mixture was cooled down to room temperature and was then precipitated using methyl alcohol. The resulting precipitate was filtered, washed with methyl alcohol several times, and then dried in a vacuum oven set to 80° C. for 24 hours, resulting in PEI (5) (yield: 85%).

POLYMER EXAMPLE 6

8 0.01 mol of octafluorobiphenylbis(dichloromaleimide), 0.01 mol of 4,4'-dihydroxy-3,3',5,5'-tetrachlorodiphenyl-1, 1-cyclohexane, 0.1 mol of anhydrous calcium oxide, $5 \times 10^{-5}$ mol of triethylamine and 5 ml of N,N-dimethylformamide were reacted under nitrogen atmosphere.

The resulting mixture was cooled down to room temperature and was then precipitated using methyl alcohol. The resulting precipitate was filtered, washed with methyl alcohol several times, and then dried in a vacuum oven set to 80° C. for 24 hours, resulting in PEI (6) (yield: 80%).

POLYMER EXAMPLE 7

0.01 mol of octafluorobiphenylbis(dichloromaleimide), 0.01 mol of 4,4'-dihydroxy-3,3',5,5'-tetrachlorodiphenyl-2, 2-propane, 0.1 mol of anhydrous calcium oxide, $5 \times 10^{-5}$ mol of triethylamine and 5 ml of N,N-dimethylformamide were reacted under nitrogen atmosphere.

The resulting mixture was cooled down to room temperature and was then precipitated usingmethyl alcohol. The resulting precipitate was filtered, washed with methyl alcohol several times, and then dried in a vacuum oven set to 80° C. for 24 hours, resulting in PEI (7) (yield: 75%).

POLYMER EXAMPLE 8

0.01 mol of octafluorobiphenylbis(dichloromaleimide), 0.01 mol of 4,4'-dihydroxydiphenyl-1,1'-diphenylmethane, 0.1 mol of anhydrous calcium oxide, $5 \times 10^{-5}$ mol of triethylamine and 5 ml of N,N-dimethylformamide were reacted under nitrogen atmosphere.

The resulting mixture was cooled down to room temperature and was then precipitated using methyl alcohol. The resulting precipitate was filtered, washed with methyl alcohol several times, and then dried in a vacuum oven set to 80° C. for 24 hours, resulting in PEI (8) (yield: 82%).

POLYMER EXAMPLE 9

0.01 mol of octafluorobiphenylbis(dichloromaleimide), 0.01 mol of 4,4'-dihydroxy-3,3'-dichlorodiphenyl-2,2-propane, 0.1 mol of anhydrous calcium oxide, $5 \times 10$ –5 mol of triethylamine and 5 ml of N,N-dimethylformamide were reacted under nitrogen atmosphere.

The resulting mixture was cooled down to room temperature and was then precipitated using methyl alcohol. The resulting precipitate was filtered, washed with methyl alcohol several times, and then dried in a vacuum oven set to 80° C. for 24 hours, resulting in PEI (9) (yield: 78%).

POLYMER EXAMPLE 10

0.01 mol of octachlorobiphenylbis(dichloromaleimide), 0.01 mol of 3,3'-difluoro-(1,1'-biphenyl)-4,4'-diol, 0.1 mol of anhydrous calcium oxide, $5 \times 10^{-5}$ mol of triethylamine and 5 ml of N,N-dimethylformamide were reacted under nitrogen atmosphere.

The resulting mixture was cooled down to room temperature and was then precipitated using methyl alcohol. The resulting precipitate was filtered, washed with methyl alcohol several times, and then diced in a vacuum oven set to 80° C. for 24 hours, resulting in PEI (10) (yield: 76%).

POLYMER EXAMPLE 11

0.01 mol of octachlorobiphenylbis(dichloromaleimide), 0.01 mol of 3,3',5,5'-tetrafluoro-(1,1'-biphenyl)-2,2'-diol, 0.1 mol of anhydrous calcium oxide, $5 \times 10^{-5}$ mol of triethylamine and 5 ml of N,N-dimethylformamide were reacted under nitrogen atmosphere.

The resulting mixture was cooled down to room temperature and was then precipitated usingmethyl alcohol. The resulting precipitate was filtered, washed with methyl alcohol several times, and then dried in a vacuum oven set to 80° C. for 24 hours, resulting in PEI (11) (yield: 74%).

POLYMER EXAMPLE 12

0.01 mol of octachlorobiphenylbis(dichloromaleimide), 0.01 mol of 2,2'-bis-(4-hydroxyphenyl)-1,3-perfluoropropane, 0.1 mol of anhydrous calcium oxide, $5 \times 10^{-5}$ mol of triethylamine and 5 ml of N,N-dimethylformamide were reacted under nitrogen atmosphere.

The resulting mixture was cooled down to room temperature and was then precipitated usingmethyl alcohol. The resulting precipitate was filtered, washed with methyl alcohol several times, and then dried in a vacuum oven set to 80° C. for 24 hours, resulting in PEI (12) (yield: 78%).

POLYMER EXAMPLE 13

0.01 mol of 2,2'-bis(trichloromethyl)-4,4'-bis(dichloromaleimide), 0.01 mol of 2,2-bis(4-hydroxy-2,3,5-trichloropheny)propane, 0.1 mol of anhydrous calcium oxide, $5 \times 10^{-5}$ mol of triethylamine and 5 ml of N,N-dimethylformamide were reacted under nitrogen atmosphere.

The resulting mixture was cooled down to room temperature and was then precipitated usingmethyl alcohol. The resulting precipitate was filtered, washed with methyl alcohol several times, and then dried in a vacuum oven set to 80° C. for 24 hours, resulting in PEI (13) (yield: 70%).

POLYMER EXAMPLE 14

0.01 mol of bis(4-dichloromaleimidetetrafluorophenyl) difluoromethane, 0.01 mol of 2,2-bis(3-hydroxyphenyl-1,3-prefluoropropane, 0.1 mol of anhydrous calcium oxide, $5 \times 10^{-5}$ mol of triethylamine and 5 ml of N,N-dimethylformamide were reacted under nitrogen atmosphere.

The resulting mixture was cooled down to room temperature and was then precipitated usingmethyl alcohol. The resulting precipitate was filtered, washed with methyl alcohol several times, and then dried in a vacuum oven set to 80° C. for 24 hours, resulting in PEI (14) (yield: 65%).

POLYMER EXAMPLE 15

0.01 mol of 2,4-bis(trifluoromethyl)difluoro-1,3-phenylenebis(dichloromaleimide), 0.01 mol of 2-bis(4-hydroxyphenyl-1,1',3,3'-chlorodifluoropropane, 0.1 mol of anhydrous calcium oxide, $5 \times^{-5}$ mol of triethylamine and 5 ml of N,N-dimethylformamide were reacted under nitrogen atmosphere.

The resulting mixture was cooled down to room temperature and was then precipitated usingmethyl alcohol. The resulting precipitate was filtered, washed with methyl alcohol several times, and then dried in a vacuum oven set to 80° C. for 24 hours, resulting in PEI (15) (yield: 68%).

Also, thermal stability, optical loss at a near infrared wavelength of 1,000~1,700 nm, and film processing property of the PEI (1) through PEI (15) synthesized by Examples 1 through 15 were measured. Here, the thermal stability of the polyamide was measured using a thermogravimetry analysis (TGA) method.

As a result, it can be ascertained that thermal stability is good in all the PEI (1) through PEI (15) from the fact that the thermal decomposition occurs at 350~450° C.

Also, it can be understood that the optical loss of the polyetherimide is similar to or less than the conventional perfluorinated polyimide.

Also, a conventional partially fluorinated or perfluorinated polyetherimide is difficult to be applied practically due to its poor film processing property. The polyetherimides obtained by Examples 1 through 15 have an improved film processing property compared to the conventional polyimide.

The polyetherimide according to the present invention has a higher refractive index than the conventional fluorinated polyimide. Thus, when using such polyetherimide as a material for a core of an optical fiber, the range of materials that can be selected for the cladding becomes wide. Also, the coating property and adhesion to a substrate are improved compared to the conventional polyimide, thereby providing a good film forming property and thermal stability.

Also, because the polyetherimide according to the present invention can minimize light loss at a near infrared wavelength range, the polyetherimide of the present invention is very useful as an optical material in the optical communications field adopting the light of near infrared wavelength. That is, the polyetherimide according to the present invention can be used as a functional polymeric material having a low optical loss characteristic which is essential for manufacturing an optical device for optical waveguiding, such as optoelectronic integrated circuit (OEIC), optoelectrical mixed wiring board (OEMWB), hybrid integration device, multi-chip module (MCM) or plastic optical fiber.

What is claimed is:

1. A composition of matter, comprising a bis(disubstitutedmaleimide) derivative represented by the chemical formula:

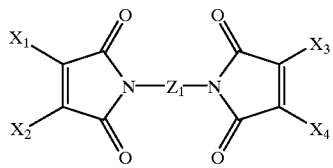

where each of $X_1$, $X_2$, $X_3$ and $X_4$ is independently selected from the group consisting of halogen atom, halogenated alkyl group, halogenated aromatic ring group, $NO_2$, $-OR^1$ and $-SR^1$ (where $R^1$ is halogenated alkyl or halogenated aromatic ring group);

and $Z_1$ is selected from the group consisting of divalent fully halogenated aliphatic hydrocarbon, divalent fully halogenated aliphatic cyclic hydrocarbon and divalent fully halogenated aromatic hydrocarbon.

2. The composition of matter of claim 1, where $X_1$ is selected from the group consisting of partially or perchlorinated alkyl groups, partially or perchlorinated aromatic ring groups, partially or perchlorinated alkoxy groups, and partially or perchlorinated phenoxy groups; and where $X_2$, $X_3$ and $X_4$ are the same as $X_1$.

3. The composition of matter of claim 1, wherein $Z_1$ is selected from the group consisting of divalent fully halogenated aliphatic hydrocarbon of $C_1$–$C_{25}$, divalent fully halogenated aliphatic cyclic hydrocarbon of $C_1$–$C_{25}$ and divalent fully halogenated aromatic hydrocarbon of $C_6$–$C_{25}$.

4. A composition of matter, comprising a bis(disubstitutedmaleimide) derivative represented by the chemical formula:

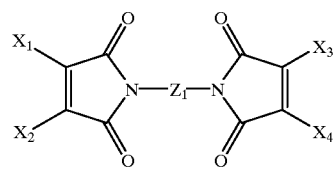

where each of $X_1$, $X_2$, $X_3$ and $X_4$ is independently selected from the group consisting of halogen atom, halogenated alkyl group, halogenated aromatic ring group, $NO_2$, $-OR^1$ and $-SR^1$ (where $R^1$ is halogenated alkyl or halogenated aromatic ring group);

and $Z_1$ is a divalent fully substituted aromatic compound.

5. The composition of matter of claim 4, where $Z_1$ is selected from the group represented by the structural formula:

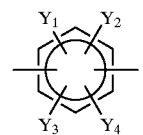

where $Y_1$, $Y_2$, $Y_3$ and $Y_4$ are independently selected from the group consisting of halogen atom, halogenated alkyl group, halogenated aromatic ring group, $NO_2$, $-OR^1$ and $-SR^1$ (where $R^1$ is a halogenated alkyl or halogenated aromatic ring group).

6. The composition of matter of claim 4, where $Z_1$ is selected from the group represented by the structural formula:

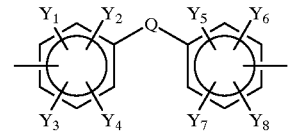

where $Y_1$, $Y_2$, $Y_3$, $Y_4$, $Y_5$ $Y_6$, $Y_7$ and $Y_8$ are independently selected from the group consisting of halogen atom, halogenated alkyl group, halogenated aromatic ring group, $NO_2$, $-OR^1$ and $-SR^1$ (where $R^1$ is halogenated alkyl or halogenated aromatic ring group); and Q represents either a single bond or is a radical selected from the group consisting of $-O-$, $-CO-$, $-SO_2-$, $-S-$, $-(OT)_m-$, $-(OT)_m-$ and $-(OT)_m-$, where T is halogenated alkylene or halogenated arylene group and m is an integer from 1 to 10.

7. A polymer for use in optical communications, comprising a repeating unit represented by the chemical formula:

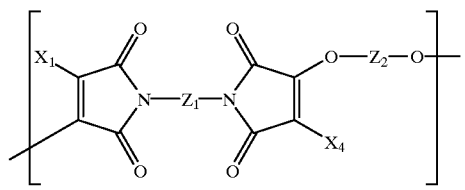

wherein $X_1$ and $X_4$ are independently selected from the group consisting of halogen atom, halogenated alkyl group, halogenated aromatic ring group, $NO_2$, $-OR^1$ and —SR¹ (where R¹ is halogenated alkyl or halogenated aromatic ring group); and $Z_1$ and $Z_2$ are independently selected from the group consisting of divalent halogenated aliphatic hydrocarbon, divalent halogenated aliphatic cyclic hydrocarbon and divalent halogenated aromatic compound.

8. The polymer of claim 7, wherein $X_1$ and $X_4$ are independently and selected from the group consisting of chloride atom, partially or perchlorinated alkyl groups, partially or perchlorinated aromatic ring groups, partially or perchlorinated alkoxy groups, and partially or perchlorinated phenoxy groups.

9. The polymer of claim 7, wherein $Z_1$ and $Z_2$ are independently selected from the group consisting of divalent halogenated aliphatic hydrocarbon of $C_1$–$C_{25}$, divalent halogenated aliphatic cyclic hydrocarbon of $C_1$–$C_{25}$ and divalent halogenated aromatic hydrocarbon of $C_6$–$C_{25}$.

10. The polymer of claim 7, wherein $Z_1$ and $Z_2$ are independently selected from the group represented by the following structural formula:

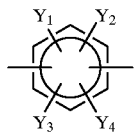

wherein $Y_1$, $Y_2$, $Y_3$ and $Y_4$ are independently selected from the group consisting of halogen atom, halogenated alkyl group, halogenated aromatic ling group, $NO_2$, —OR¹ and —SR¹ (where R¹ is halogenated alkyl or halogenated aromatic ring group).

11. The polymer of claim 7, wherein $Z_1$ and $Z_2$ are independently selected from the group represented by the following structural formula:

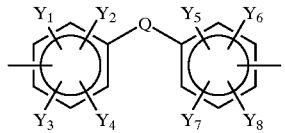

wherein $Y_1$, $Y_2$, $Y_3$, $Y_4$, $Y_5$, Y6, $Y_7$ and $Y_8$ are independently selected from the group consisting of halogen atom, halogenated alkyl group, halogenated aromatic ring group, $NO_2$, —OR¹ and —SR¹ (where R¹ is halogenated alkyl or halogenated aromatic ling group); and Q is a simple chemical bond or selected from the group consisting of —O—, —CO—, —$SO_2$—, —S—, —(OT)$_m$—, —(OT)$_m$— and —(OT)$_m$— (where T is halogenated alkylene or halogenated arylene group and m is an integer from 1 to 10).

12. The polymer of claim 7, where the polymer has a molecular weight of $1 \times 10^4$~$4.5 \times 10^4$ Dalton.

13. The polymer of claim 7, where the polymer has a thermal decomposition temperature of 300~500° C.

14. The polymer of claim 7, where the polymer has a glass transition temperature of 220~320° C.

15. A polymer prepared by the process of polymerization of a bis(disubstitutedmaleimide) derivative with a diol, where:

said bis(disubstitutedmaleimide) derivative is selected from the group consisting of 2,3,5,6-tetrafluorobenzenebis(dichloromaleimide), 2,3,5,6-tetrachlorobenzenebis(dichloromaleimide), octafluorobiphenylbis(dichloromaleimide), 2,2'-bis(trichloromethyl)-4,4'-bis(dichloromaleimide)hexafluorobiphenyl, bis(4-dichloromaleimidetetrafluorophenyl)difluoromethane, 2,4-bis (trifluoromethyl)difluoro-1,3-phenylenebis(dichloromaleimide), bis(dichloro-4-maleimide) and bis(3,4-dichloromaleimide)octafluorobiphenylsulfone.

16. A polymer prepared by the process of polymerization of a bis(disubstitutedmaleimide) derivative with a diol, where:

said diol is selected from the group consisting of tetrafluorohydroquinone, tetrachlorohydroquinone, 2,2-bis(4-hydroxyphenyl)hexachloropropane, 4,4'-dihydoroxydiphenylether, 4,4'-dihydroxydiphenylsulfone, 4,4'-dihydroxy-3,3',5,5'-tetrachlorodiphenyl-1,1-cyclohexane, 4,4'-dihydroxy-3,3',5,5'-tetrachlorodiphenyl-2,2-propane, dihydroxydiphenyl-1,1'-diphenylmethane, 4,4'-dihydroxy-3,3'-dichlorodiphenyl-2,2-propane, difluoro-(1,1'-biphenyl)-4,4-diol, 3,3',5,5'-tetrafluoro-(1,1'-biphenyl)-2,2'-diol, 2,2'-bis-(4-hydroxyphenyl-1,3-perfluoropropane, 2,2-bis(4-hydroxy-2,3,5-trichlorophenyl)propane, 2,2-bis(3-hydroxyphenyl-1,3-perfluoropropane), and 2-bis(4-hydroxyphenyl-1,1',3,3'-chlorodifluoropropane).

* * * * *